United States Patent [19]
Zalisz et al.
[11] 4,412,946
[45] Nov. 1, 1983

[54] IMMUNOSTIMULATING GLYCOPROTEINS

[75] Inventors: René Zalisz, Saint Ouen l'Aumone; Marie-France Salles, Paris, both of France

[73] Assignee: Roussel Uclaf, Paris, France

[21] Appl. No.: 300,910

[22] Filed: Sep. 10, 1981

[30] Foreign Application Priority Data

Sep. 19, 1980 [FR] France ............ 80 20188

[51] Int. Cl.[3] ............ A61K 37/02; A61K 39/108; A61K 39/40; C07G 7/00

[52] U.S. Cl. ............ 260/112 R; 424/92; 424/85; 424/87; 424/88

[58] Field of Search ............ 260/112 R; 424/92

[56] References Cited

U.S. PATENT DOCUMENTS 3,408,440 10/1968 Voss ............ 424/92
3,855,197 12/1974 Hirsch et al. ............ 260/112 R X
3,929,994 12/1975 Hirsch et al. ............ 260/112 R X
3,956,481 5/1976 Jolles et al. ............ 424/92
4,001,395 1/1977 Jolles et al. ............ 424/92
4,013,788 3/1977 Jolles et al. ............ 424/177
4,108,849 8/1978 Thomas ............ 424/95
4,154,821 5/1979 Drouet et al. ............ 435/68 X
4,297,272 10/1981 D'Hinterland et al. ............ 260/112 R
4,356,171 10/1982 Zalisz et al. ............ 260/112 R X

*Primary Examiner*—Howard E. Schain
*Attorney, Agent, or Firm*—Hammond & Littell, Weissenberger and Muserlian

[57] ABSTRACT

Novel water-soluble, immunostimulating glycoproteins extracted from *Klebsiella pneumoniae* containing 30 to 45% by weight of proteins, 30 to 40% by weight of neutral saccharides, up to 4% by weight of glucuronic acid, 2 to 5% by weight of osamines and having a molecular weight of about 350,000 daltons.

2 Claims, No Drawings

IMMUNOSTIMULATING GLYCOPROTEINS

STATE OF THE ART

U.S. Pat. Nos. 3,855,197 and 3,929,994 describe a number of glycoprotein extracts including one extracted from *Klebsiella pneumonia* having anti-inflammatory activity.

OBJECTS OF THE INVENTION

It is an object of the invention to provide novel water-soluble glycoproteins extracted from *Klebsiella pneumonia* and a process for their preparations.

It is another object of the invention to provide novel immunostimulating compositions and to a novel method of inducing immunostimulating activity in warm-blooded animals.

These and other objects and advantages of the invention will become obvious from the following detailed description.

THE INVENTION

The novel products of the invention are water-soluble, immunostimulating glycoproteins extracted from *Klebsiella pneumoniae* containing 30 to 45% by weight of proteins, 30 to 40% by weight of neutral saccharides, up to 4% by weight of glucuronic acid, 2 to 5% by weight of osamines and having a molecular weight of about 350,000 daltons.

The neutral saccharides in the compositions are neutral hexoses such as glucose, mannose or galactose. The molecular weight of the glycoproteins are estimated by by ultracentrifugation.

The glycoproteins of the invention are extracted from various strains of *Klebsiella pneumoniae* which are freely available from various microorganism depositories but the preferred strain is No. 52,145 deposited at the Pasteur Institute of Paris, France.

The study of the structure of the glycoproteins is determined by different chemical techniques, notably reduction of uronic acid residues by carbodiimide, permethylation, uronic degradation, periodic oxidation or chromic oxide oxidation to determine the precise composition. The glycoproteins of the invention are formed as a proteic chain which is attached to a polysaccharide fraction.

The preferred glycoproteins of the invention are those wherein the protein fraction contains about 30% of the acid amino acids which are amino acids such as aspartic acid or glutamic acid and those wherein the polysaccharide fraction contains about one molecule of glucose and 4 molecules of galactose. Especially preferred are those glycoproteins wherein the polysaccharide fraction is essentially comprised of repeating polysaccharide units of the following structures

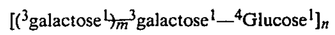

$[(^{3}\text{galactose}^{1})_{\overline{m}}{}^{3}\text{galactose}^{1}\text{—}^{4}\text{Glucose}^{1}]_n$ wherein m is 3,4 or 5 and it has been determined that in this structure n is a number equal to or slightly different from 94 when m is 5.

The novel process of the invention for the preparation of the said glycoproteins comprises treating a solution of glycoproteins obtained by diafiltration of an extract of a lysate of *Klebsiella pneumoniae* culture with a quaternary ammonium compound, isolating a surnageant by removal of the resulting precipitate, treating surnageant corresponding to a saline solution of glycoproteins in the cold with a low molecular weight alkanol, recovering the resulting precipitate, dissolving the precipitate in water and subjecting the resulting solution to dialysis and then lyophilisis, dissolving the product, filtering the solution through a gel, recovering the first eluted fraction and concentrating the eluant, optionally to dryness.

The starting solutions of glycoproteins may be obtained from various sources such as diafiltration of lysates of *Klebsiella pneumoniae* cultures with calibrated porous membranes capable of retaining molecules with a molecular weight equal to or greater than a given molecular weight which is a constant for the membranes.

The membranes used may be, for example, those membranes sold under the name Amicon XM50, PM30 and UM2 but the preferred membranes are those having a retention of 100,000 daltons such as the membranes sold under the Amicon marks XM100 or H1 P100. The most preferred membranes are those which retain molecules with a molecular weight greater than 300,000 daltons such as membrane sold under the mark XM300 by Amicon and Romicon.

The diafiltration permits a selection in solution of molecules with a molecular weight greater than a given molecular weight which is determined by the choice of the membrane as a function of the desired retention. It is evident to a man skilled in the art which uses solutions of the same characteristics obtained by the other means such as by chromatography with polymerized hydrophilic gel is always possible.

Prior to this selection operation, the lysate has very advantageously, been delipided and is free of nucleic acids.

Under the preferred operating conditions of the process of the invention, the starting solution of glycoproteins is obtained by the process of U.S. Pat. No. 3,929,994 and the molecular weight of glycoproteins is estimated by the gel exclusion technique.

The quaternary ammonium compounds used to treat the starting glycoprotein solution may be, for example, halides such as pyridylcetylammonium chloride and especially trimethylcetylammonium bromide known as Cetavlon.

The precipitate formed as a result of the quaternary ammonium treatment is separated from the surnageant by classical methods such as decantation or filtration, but preferably by centrifugation.

The surnageant solution is then treated cold, about +4° C., with a low molecular weight alkanol such as methanol, ethanol, isopropanol and n-propanol, preferably ethanol. Very interesting results are obtained by using six volumes of ethanol per volume of saline solution overnight at a temperature of about +4° C.

The precipitate is redissolved in water and subjected to dialysis for purification which is effected with the classical type membrane cells with for example, cellulose or collodion membranes. The preferred cells use membranes of regenerated cellulose with an average pore diameter of about 24 A° which retains substances with a molecular weight greater than 12 to 14,000 daltons. Among suitable dialysis cells are preferably Visking tube cells. The said dialysis removes low molecular weight impurities as traces of alkanol from the glycoprotein solution. It is obvious that the glycoproteins of the invention are less pure without the dialysis step. The concentration to dryness may be effected by classical methods such as atomization or lyophilization.

The lyophilization is effected by classical methods such as in a congelator-sublimator of average size such as commercial models SMU or SMRG of Usifroid Company or lyophilizator of large size such as the apparatus formed by a CA-1 congelator and a SMIRS sublimator, both commercially available from Usifroid. The smaller laboratory models as well as other commercial models such as those sold by Serail may be used. The steps of lyophilization are optional but are still preferred.

The gel filtration is directly realized after dissolution of the lyophilizate in the water or using the aqueous solution of glycoproteins. Preferably, the solution is buffered and filtered and elution is effected with the same buffer which is preferably ammonium carbonate in such a manner so that the glycoprotein solution titers 0.1 M of buffer.

The filtration gels useful for the process may be those commercially available under the name Sephadex, most preferably Sephacryl S 300 and especially Ultragel ACA 34. The filtration may be controlled by classical procedures, especially by use of ultraviolet spectrography at 238 nm.

In a preferred mode of the process of the invention, the quaternary ammonium compound is trimethylcetylammonium bromide and centrifugation is used to isolate the surnageant and the lower alkanol is ethanol, the filtration gel is Ultragel ACA 34 and the eluted fraction is dried by lyophilization.

The novel immunostimulating compositions of the invention are comprised of an immunostimulating effective amount of at least one glycoprotein of the invention and a pharmaceutical carrier or excipient. The compositions may be in the form of tablets, dragees, gelules, granules, solutions, syrups, suppositories, lyophilized or non-lyophilized injectable preparations, ovules, creams, pomades, lotions, drops, collyriums or aerosols prepared in the usual manner.

Examples of suitable excipients are talc, arabic gum, lactose, starch, magnesium stearate, cacao butter, aqueous or non-aqueous vehicles, fatty bodies of animal or vegetables origin, paraffinic derivatives, glycols, diverse wetting agents, dispersants or emulsifiers and preservatives.

The compositions have a remarkable immunostimulating activity as well as a very good tolerance to warm-blooded animals. They are useful for the treatment or prevention of infectious maladies caused by bacteria or virus, for the treatment of parasitic maladies, for toxic infections, in the treatment of post-hospitalized or post-surgical infections.

The novel method of the invention of inducing immunostimulating activity in warm-blooded animals, including humans, comprises administering to warm-blooded animals an amount of a glycoprotein of the invention in an amount sufficient to induce immunostimulating activity. The glycoproteins may be administered orally, rectally, parenterally, or topically and the effective amount will vary on the cause of the affections and the subject but may be 0.005 to 0.3 mg/kg. For example, when administered orally, the effective amount may be 0.02 to 0.3 mg/kg per day; rectally, the effective amount may be 0.02 to 0.3 mg/kg per day; and parenterally, the effective amount may be 0.005 to 0.1 mg/kg per day.

In the following examples there are described several preferred embodiments to illustrate the invention. However, it is to be understood that the invention is not intended to be limited to the specific embodiments.

EXAMPLE 1

20 g of the product of Example 8 of U.S. Pat. No. 3,929,994 were dissolved in 2 liters of permuted water and then 1.6 liters of a 3% Cetavlon solution was slowly added thereto. The mixture was stirred for one hour and was then centrifuged at 10,000 rpm for 15 minutes to remove the precipitate. 3 liters of 95% ethanol were added to the surnageant over 15 minutes and the mixture was stirred for one hour and centrifuged at 10,000 rpm for 15 minutes. The surnageant was removed and the precipitate was dissolved in one liter of water. The solution was subjected to dialysis for 48 hours in Visking tubes against permuted water at 4° C. and the resulting solution was lyophilized to obtain 6.2 g of water-soluble glycoproteins, 1 g of which was dissolved in 10 ml of 0.1 M ammonium carbonate solution. The resulting solution was passed through a column with a diameter of 2.5 cm and containing 1 liter of Ultragel ACA 34 and elution was effected with 0.1 M ammonium carbonate solution. The fraction corresponding to a first elution peak detected with U.V. at 280 nm was recovered and lyophilized to obtain 0.51 g of a purified water-solution glycoprotein containing 30 to 45% by weight of weight of protein, 30 to 40% by weight of neutral saccharides, 2 to 5% by weight of osamines and a molecular weight of about 350,000 daltons.

EXAMPLE 2

0.800 liters of a 3% Cetavlon solution was added with stirring to a solution of 20 g of the glycoprotein of Example 1 of U.S. Pat. No. 3,929,994 in one liter of permuted water and the mixture was stirred for one hour and the centrifuged at 10,000 rpm for 15 minutes. The surnageant was admixed with 1.5 liters of 95% ethanol and the mixture was stirred for one hour and was centrifuged at 10,000 rpm for 15 minutes. The precipitate was dissolved in 0.500 liters of water and the solution was subjected to dialysis for 48 hours in Visking tubes against permuted water at 4° C. The resulting solution was lyophilized to obtain 6.5 g of glycoprotein which was passed through Ultragel ACA 34 by the technique of Example 1 to obtain 3.28 g of water-soluble glycoprotein of the invention.

EXAMPLE 3

Tablets were prepared containing 5 mg of the glycoproteins of Example 1 and sufficient excipient of lactose, starch, talc and magnesium stearate for a final tablet weight of 100 mg.

A pomade was prepared from 200 mg of the glycoproteins of Example 2 and sufficient excipient for a final weight of 100 g.

PHARMACOLOGICAL DATA

A. Immunostimulating and Mitogenic Activity

40 μg of the test compound and 40 μg of bovine albumin serum were administered intraplantary to groups of 10 mice and 10 days later, the mice received intraveinously a non-lethal and non-shocking 100 μg of Serum-albumin. The controls received only serum-albumin in the first injections. The immunostimulating activity was measured as the increase to the reponse of anaphylactic shock to Serum-albumin and the mitogenic activity was measured by the increase in ganglion weight draining at the point of injection.

The immunostimulating activity was determined by checking the number of animals presenting a state of shock (dyspnea with muzzle cyanosis up to paralysis of rear train, convulsions and death) as well as the dead, 2 hours after the intravenous injection of Serum-albumin. The results are reported in Table I.

TABLE 1

| Product of Example | % of Shocked animals | % dead animals |
|---|---|---|
| 1 | 60 | 40 |
| 2 | 100 | 50 |
| controls | 0 | 0 |

To determine the mitogenic activity, the surviving animals were killed 2 hours after the intravenous injection of Serum-albumin were taken the popliteal ganglions draining the paw where the injection was and the weight was controlled. The mitogenic activity expressed with index corresponding to the ratio of average weight of ganglion of animal treated with the test product and the control animals treated only with Serum-albumin and the results are reported in Table II.

TABLE II

| Product of Example | Index |
|---|---|
| 1 | 9.1 |
| 2 | 7.2 |

The tests show that the products of Examples 1 and 2 have a very good immunostimulating and mitogenic activity.

B. Stimulation of Non-Specific Defenses

This stimulation was studied by the clearance test of carbon on mice inspired by the technique of Halpern which consisted of injecting an animal in the ocular sinus with a suspension of colloidal carbon and determining as a function of time the kinetics of the disappearance of carbon in the blood effected by measuring the optic density. The products were administered intraperitoneally 24 and 48 hours before the test and the results were expressed as percentage of elimination of carbon particles as compared to controls receiving only the colloidal carbon injection which corresponded to 100% of the number of carbon particles. The results are reported in Table III.

TABLE III

| Product of Example | Dose in mg/kg | % activity - minutes after injection | |
|---|---|---|---|
| | | 8 | 30 |
| 1 | 0.25 | 50% | 70% |
| 2 | 0.25 | 50% | 70% |

Examination of the results show that the two products provoked an intense stimulation of the defenses of the organism.

C. Acute Toxicity

The $DL_{50}$ dose or dose which killed 50% of mice receiving the product intraperitoneally was determined by the Behrens and Karber method and was 30 mg/kg for the glycoproteins of Examples 1 and 2.

D. Tolerance

The subcutaneous injection of 0.2 ml of the glycoproteins of Examples 1 and 2 at a dose of 1000 $\gamma$/kg in mice did not cause any local or general intolerance.

Various modifications of the products and processes of the invention may be made without departing from the spirit or scope thereof and it is to be understood that the invention is intended to be limited only as defined in the appended claims.

What is claimed is:

1. A process for the preparation of a water-soluble immunostimulating glycoprotein extracted from *Klebsiella pneumoniae* containing 30 to 45% by weight of proteins, 30 to 40% by weight of neutral saccharides, up to 4% by weight of glucuronic acid, 2 to 5% by weight of osamines and having a molecular weight of about 350,000 daltons comprising treating a solution of glycoproteins obtained by diafiltration of an extract of a lysate of *Klebsiella pneumoniae* culture with a quaternary ammonium compound, isolating a surnageant by removal of the resulting precipite, treating surnageant corresponding to a saline solution of glycoproteins in the cold with a lower molecular weight alkanol, recovering the resulting precipitate, dissolving the precipitate in water and subjecting the resulting solution to dialysis and then lyophilysis, dissolving the product, filtering the solution through a gel, recovering the first eluted fraction and concentrating the eluant, optionally to dryness.

2. The process of claim 1 wherein the quaternary ammonium compound is trimethylcetylammonium bromide, the surnageant is obtained by centrifugation and the low molecular weight alkanol is ethanol, the gel is Ultragel ACA 34 and the eluted fraction is dried by lyophilization.

* * * * *